(12) United States Patent
Sholtis et al.

(10) Patent No.: US 7,983,934 B1
(45) Date of Patent: Jul. 19, 2011

(54) METHOD AND SYSTEM FOR COLLABORATIVE PERSONAL HEALTH HISTORY

(75) Inventors: Steven A. Sholtis, El Dorado Hills, CA (US); Patricia Keaney, Greenbrae, CA (US); Lisa A. Voss, San Jose, CA (US)

(73) Assignee: Intuit Inc., Mountain View, CA (US)

( * ) Notice: Subject to any disclaimer, the term of this patent is extended or adjusted under 35 U.S.C. 154(b) by 1014 days.

(21) Appl. No.: 11/796,627

(22) Filed: Apr. 26, 2007

(51) Int. Cl.
*G06Q 50/00* (2006.01)
(52) U.S. Cl. .......................................... 705/2
(58) Field of Classification Search ........................ 705/2
See application file for complete search history.

(56) References Cited

U.S. PATENT DOCUMENTS

| 7,194,426 B1 * | 3/2007 | Box .................................. 705/26 |
| 7,698,154 B2 * | 4/2010 | Marchosky ........................ 705/3 |
| 2007/0005394 A1 * | 1/2007 | Bleyendaal et al. ............... 705/2 |
| 2007/0078687 A1 * | 4/2007 | Dettinger et al. ................ 705/3 |
| 2007/0197882 A1 * | 8/2007 | Smith et al. ..................... 600/300 |

OTHER PUBLICATIONS

Potamias, G., et al., "Role-based access to patients' clinical data: the InterCare approach in the region of Crete", IOS Press, Amsterdam, 2000, pp. 1074-1079.*
"The Power Behind Your Records"; Medic Alert Magazine; vol. 3, Issue 2; Apr. 1, 2006; (13 pages).

* cited by examiner

*Primary Examiner* — Luke Gilligan
*Assistant Examiner* — Robert Sorey
(74) *Attorney, Agent, or Firm* — Osha • Liang LLP (57) ABSTRACT

A method for healthcare collaboration that includes granting access, across a network, to a portion of a personal health history (PHH) account associated with a patient, wherein access is granted to a healthcare provider and controlled by the patient, submitting healthcare data to the portion of the PHH account based on a health service received by the patient from the healthcare provider, and transfer the healthcare data for review.

15 Claims, 6 Drawing Sheets

METHOD AND SYSTEM FOR COLLABORATIVE PERSONAL HEALTH HISTORY

BACKGROUND

Throughout an individual's lifetime, an individual may be under the care of numerous healthcare providers. For example, an individual may be treated by a pediatrician during childhood, by a family practice doctor to maintain physical health, a dentist to maintain healthy teeth, an ophthalmologist to maintain healthy eyes, an orthopedist to correct bone fractures and other orthopedic problems, and visit various other healthcare providers. Further, the individual may have one or more surgeries, visit an emergency room, and have a variety of x-rays and other such lab treatments and/or tests.

Typically, upon the first visit to a healthcare provider, the individual or a guardian for the individual is given a form to enter the individual's personal health history. The personal health history typically includes data such as types and dates of surgeries, names and types of illnesses, medications, medical history of parents and grandparents, etc. After submitting the data in the form, the healthcare provider creates a medical record for the patient. The healthcare provider's medical record for the patient contains the personal health history entered on the form as well as a history of the patient's interaction with the healthcare provider.

Because each healthcare provider typically creates a separate medical record from other healthcare providers, the individual or their guardian is responsible for monitoring the individual's personal health history and ensuring that healthcare providers treating the patient are aware of changes in their personal health history affecting the healthcare of the individual.

SUMMARY

In general, in one aspect, the invention relates to a method for healthcare collaboration that includes granting access, across a network, to a portion of a personal health history (PHH) account associated with a patient, wherein access is granted to a healthcare provider and controlled by the patient, submitting healthcare data to the portion of the PHH account based on a health service received by the patient from the healthcare provider, and transfer the healthcare data for review.

In general, in one aspect, the invention relates to a method for healthcare collaboration that includes granting access, across a network, to a portion of a personal health history (PHH) account associated with a patient, wherein access is granted to a healthcare provider and controlled by the patient, submitting healthcare data to the PHH account by the healthcare provider accessing the portion of the PHH account, and transferring the healthcare data to the patient for review.

In general, in one aspect, the invention relates to a method for healthcare collaboration that includes granting access, across a network, to a portion of a personal health history (PHH) account associated with a patient, wherein access is granted to a first healthcare provider and controlled by the patient, reviewing the healthcare data in the PHH account by the first healthcare provider accessing the portion of the healthcare data, wherein the healthcare data is submitted by a second healthcare provider accessing the PHH account, and modifying health service performed on the patient using the healthcare data in the PHH account.

In general, in one aspect, the invention relates to a system for healthcare collaboration that includes a personal health history (PHH) repository for storing a PHH account associated with a patient, and a PHH engine configured to grant access, across a network, to a portion of the PHH account associated with the patient, wherein access is granted to a healthcare provider responsive to a request of the patient, populate the PHH account with healthcare data, wherein the healthcare data is submitted based on a health service received by the healthcare provider, and display the healthcare data when the healthcare provider accesses the portion of the PHH account.

In general, in one aspect, the invention relates to a system for healthcare collaboration a personal health history (PHH) repository for storing a PHH account associated with a patient, and a PHH engine configured to grant access, across a network, to a portion of a personal health history (PHH) account associated with a patient, wherein access is granted to a first healthcare provider and controlled by the patient, and display the healthcare data in the PHH account to the first healthcare provider accessing the portion of the healthcare data, wherein the healthcare data is submitted by a second healthcare provider accessing the PHH account.

In general, in one aspect, the invention relates to a computer readable medium that includes instructions to perform granting access, across a network, to a portion of a personal health history (PHH) account associated with a patient, wherein access is granted to a healthcare provider and controlled by the patient, submitting healthcare data to the portion of the PHH account based on a health service received by the patient from the healthcare provider, and transfer the healthcare data for review.

In general, in one aspect, the invention relates to a computer readable medium that includes instructions to perform granting access, across a network, to a portion of a personal health history (PHH) account associated with a patient, wherein access is granted to a healthcare provider and controlled by the patient, submitting healthcare data to the PHH account by the healthcare provider accessing the portion of the PHH account, and transferring the healthcare data to the patient for review.

Other aspects of the invention will be apparent from the following description and the appended claims.

DETAILED DESCRIPTION

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention provide a method and system for healthcare collaboration of a patient using the patient's personal health history (PHH). Specifically, embodiments of the invention use a patient's PHH account, which may be accessed by the patient and the healthcare providers. The PHH account provides a method of communicating healthcare data between a patient and a healthcare provider and thereby provides a method for healthcare collaboration. In one or more embodiments of the invention, healthcare data includes medical data used for the treatment of a patient.

Figure 1:
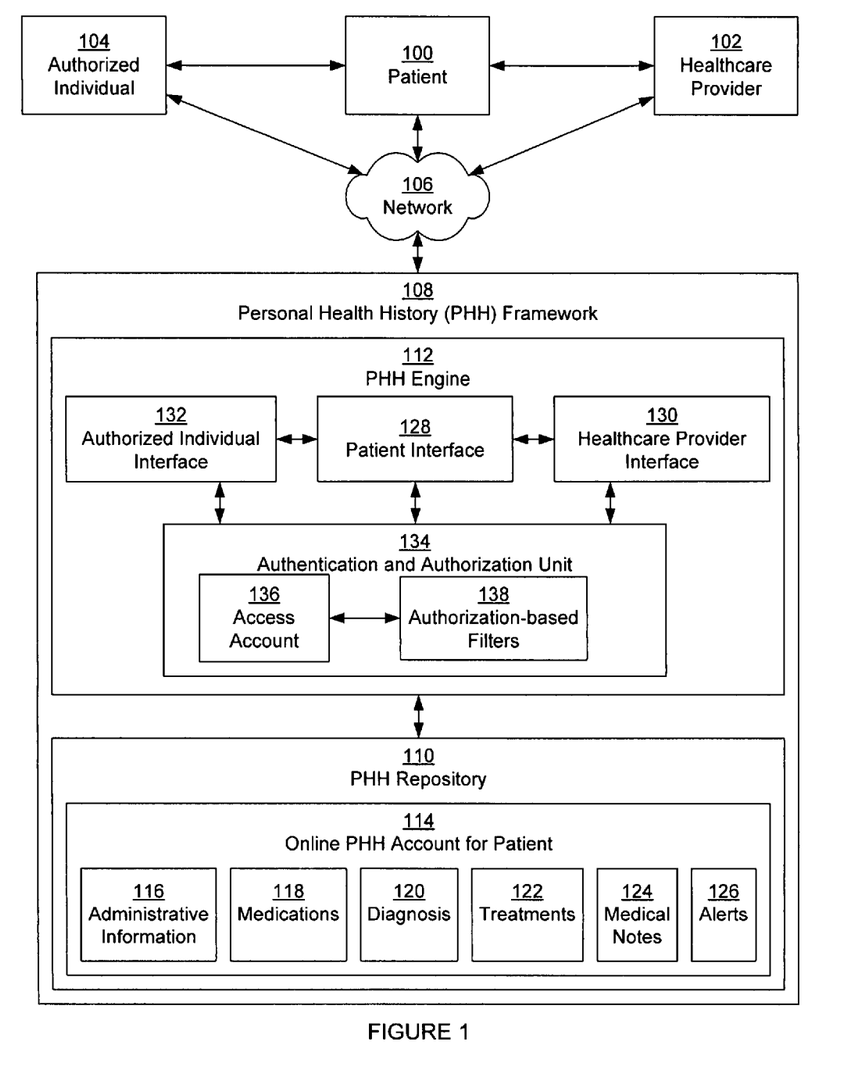
FIG. 1 shows a schematic diagram of a system for collaborative personal health history in accordance with one or more embodiments of the invention.

FIG. 1 shows a schematic diagram of a system for collaborative personal health history in accordance with one or more embodiments of the invention. As shown in FIG. 1, the system includes a patient (100), a healthcare provider (102), an authorized individual (104), a network (106), and a PHH framework (108). Each of these components is described below.

A patient (100) is any individual which at some point in time is under the care of a healthcare provider (102) in one or more embodiments of the invention. For example, a patient may be a person who receives a surgery, has an office visit with a healthcare provider, fills a prescription, receives medical tests, requires emergency care, etc. Further, for the purposes of the description, a patient (100) may also be considered to access and interact with the healthcare framework when a guardian (or other authorized individual (104)) of the patient accesses and interacts with the healthcare framework on behalf of the patient. A guardian is an authorized individual or entity that may or may not have medical power of attorney to act on behalf of the patient. Typically, a guardian exists when the patient is somehow incapacitated, such as because of age or disability.

A healthcare provider (102) is any individual or entity that provides a health service of any kind. For example, a healthcare provider (102) may be a physician, nurse, hospital, pharmacist, therapist, dentist, medical assistant, traditional therapy practitioner, lab technician, a clinic, a paramedic, a medical technician, or any other provider of a health service. In one or more embodiments of the invention, if a patient is treated by multiple healthcare providers, then the healthcare providers may or may not be associated with each other. Specifically, the healthcare providers may belong to the same managed care group and network or to different managed care groups and networks. For the purposes of the description, a healthcare provider (102) is considered to interact with the PHH framework when an assistant of the healthcare provider (102) interacts with the PHH framework on behalf of the healthcare provider (102).

In addition to the healthcare provider (102), the patient (100) is also connected to an authorized individual (104) in accordance with one or more embodiments of the invention. An authorized individual (104) is any individual that is, in some manner, related to the patient (100) and may desire knowledge of the healthcare of the patient. For example, a authorized individual (104) may be a spouse, significant other, relative, friend, support group member, guardian, or any other individual having personal knowledge of the patient and his/her condition.

In one or more embodiments of the invention, the patient (100), healthcare provider (102), and authorized individual (104) are connected to a network (106). The network (106) may be a local area network (LAN) or a wide area network (e.g., the Internet), wireless network, telephone networks, mobile networks, and other communication mediums or combinations thereof. Specifically, in one or more embodiments of the invention, the patient (100), healthcare provider (102), and the authorized individual (104) may access a PHH framework (108) using the network (106). One skilled in the art will appreciate that the PHH framework (108) may also accessed either online (i.e., connected to the network) or offline (i.e., away from the network either temporarily or for a period of time). If accessed offline, then the PHH framework (108) include functionality to synchronize information when online access is restored.

A PHH framework (108) includes functionality to maintain and permit access to a patient's PHH. The PHH framework (108) may be maintained on a single computer system, such as a server, or distributed across multiple computer systems of various kinds. The PHH framework (108) includes a PHH repository (110) and a PHH engine (112) in accordance with one or more embodiments of the invention.

A PHH repository (110) is a storage unit (e.g., a file system, database, directory server, or any other type of storage mechanism for data) for maintaining a patient's PHH in accordance with one or more embodiments of the invention. A patient's PHH is maintained as healthcare data in a PHH account (114) in the PHH repository (110). Specifically, the PHH account for the patient (114) is an organized storage system for maintaining healthcare data that is a part of the PHH of the patient. Moreover, the PHH account is remotely accessible by the patient (100), healthcare provider (102), and authorized individual (104). The healthcare data in the PHH account (114) may include administrative information (116), medications (118), diagnosis (120), treatments (122), medical notes (124), alerts (126), as well as any other type of healthcare data that is a part of the PHH of a patient. Each of the aforementioned types of healthcare data is described below.

Administrative information (116) is information about the patient (100) in accordance with one or more embodiments of the invention. For example, administrative information (116) may include address and contact information, health insurance information, emergency contact information, PHH account preferences, etc.

Medications (118) may include current and past medications for the patient including both prescription and non-prescription medications. Additionally, medications (118) may specify dosage specifics such as amount and time for administering the medications. Further, medications (118) may be divided into categories, such as required medications (e.g., insulin) and optional medications (e.g., vitamins).

Diagnosis (120) is information regarding the current and past conditions affecting the patient (100). For example, a diagnosis may be an illness, affliction, or special capability of the patient (100). A diagnosis (120) may be stored with or separately from corresponding treatments (122). Treatments (122) include any mechanism for preventing or alleviating healthcare related conditions. For example, treatments may include data related to therapy, medication regimen, surgeries performed, etc.

Further, the PHH account (114) for the patient may also include medical notes (124). Medical notes (124) are additional healthcare data that may be provided by the patient (100) and/or the healthcare provider (102). For example, medical notes (124) may include lab results and interpretation of lab results, blood pressure monitoring information, patient temperature, general wellness information, pain information, etc. Further, medical notes (124) may also include information about the personal health history of family members of the patient, such as illnesses afflicting a parent or grandparent of the patient. For example, the medical notes may include history of cancer, diabetes, or other conditions which elevate the patient's probability of having the condition when a family member is afflicted with the condition.

In one or more embodiments of the invention, alerts (125) inform the patient (100) and healthcare provider (102) about changes in the PHH account (114). An alert may be created to inform the patient when a healthcare provider has accessed the PHH account and whether the healthcare provider has added new healthcare data to the PHH account. For example, if a healthcare provider reviews a lab result for the patient, the healthcare provider may create a medical note detailing an analysis of the lab result. In the example, the creation of the medical note may cause the generation of the alert. Alternatively, rather than storing the alerts (125), the alerts may be generated and immediately transmitted to patient or healthcare provider before being discarded.

In one or more embodiments of the invention, the PHH account for a patient (114) is stored in a manner such that the patient may grant access to only portions of the PHH account. Specifically, individual portions of the PHH may have a security code to specify who has permission to access the portion of the healthcare data. For example, the security code may be a list of identifiers of groups of healthcare providers, individuals that may access the portion of healthcare data, or any other indication of who has access. Different types of security mechanisms exist that have corresponding security codes for securing the portions of an online account without granting access to other portions any number of which may be used. For example, the security code may be configured to allow a patient to grant a hospital access to required medications without granting the hospital access to optional medications.

Continuing with FIG. 1, the PHH repository (110) is connected to a PHH engine (112) in accordance with one or more embodiments of the invention. A PHH engine (112) includes functionality to provide an interface to the PHH repository (110). Specifically, a PHH engine includes role-specific interfaces (e.g., patient interface (128), healthcare provider interface (130), authorized individual interface (132)) and an authentication and authorization unit (134).

From the perspective of the PHH framework (108), each user accessing the PHH framework (108) has a role with respect to the PHH account of the patient (114). A role is the position of the user accessing the PHH repository. For example, a role of a user may be that of a patient, a healthcare provider, or an authorized individual. Each role has a role-specific interface (e.g., patient interface (128), healthcare provider interface (130), authorized individual interface (132)). The role specific interface (e.g., patient interface (128), healthcare provider interface (130), authorized individual interface (132)) provides access to the PHH repository according to the perspective (i.e., needs) of the role.

Specifically, a patient interface (128) allows the patient to access their PHH account and grant or deny access to authorized individuals and healthcare providers. A patient interface (128) may allow a patient to view and update the patient's PHH. In one or more embodiments of the invention, the patient interface (128) may allow the patient to interact with the patient's PHH by categories of healthcare data in the PHH. For example, the categories may be based on the age of the patient at the time the PHH entry is created (e.g., child, 20-29 years old, etc.), bodily system affected (e.g., skeletal, digestive, nervous, etc.), healthcare provider treating patient, specialty of a physician, or any other grouping of healthcare data in the PHH.

In contrast to a patient interface (128), a healthcare provider interface (130) enables a healthcare provider (102) to access the PHH repository (110). In one or more embodiments of the invention, the healthcare provider interface (130) includes a mechanism for a healthcare provider (102) to select a patient from a patient list of those patients under the care of the healthcare provider (102) and interact with the portion of the patient's PHH granted by the patient (100). The healthcare provider interface (130) may further allow the healthcare provider (102) to update the patient's PHH account (114). Thus, healthcare data may be communicated between the healthcare provider (102) and the patient (100) using the PHH engine (112).

An authorized individual interface (132) is an interface for an authorized individual (104) to access the PHH account of the patient (100). Specifically, an authorized individual interface (132) displays a portion of the PHH account for the patient to the authorized individual (104). In one or more embodiments of the invention, the authorized individual interface (132) prevents the authorized individual (104) from modifying the PHH account of the patient (114). Alternatively, the modification of the patient's PHH account (114) by the authorized individual (104) may be configurable to allow greater access according to the situation encountered.

Each role specific interface (e.g., patient interface (128), healthcare provider interface (130), authorized individual interface (132)) includes functionality to access the PHH repository (110) using an authentication and authorization unit (134) in one or more embodiments of the invention. An authentication and authorization unit (134) includes functionality to secure the patient's PHH. Specifically, an authentication and authorization unit (134) prevents unauthorized access to the PHH repository (110). Moreover, the authentication and authorization unit (134) includes functionality to authenticate a user and ensure that the user is authorized to perform the actions requested by the user.

The authentication and authorization unit (114) includes an access account (136) for each user (e.g., patient (100), healthcare provider (102), authorized individual (104)) in one or more embodiments of the invention. An access account (136) may include authentication information (e.g., login information), user preferences, administrative information (e.g., role of user, address information, etc.), and authorization information for the user (e.g., information which specifies data that the user may access).

The access account (136) is connected to an authorization based filter (138) in one or more embodiments of the invention. An authorization based filter (138) includes functionality to ensure that the user is authorized to access data from the PHH account for the patient (114) and sent to the user. Specifically, in one or more embodiments of the invention, the authorization based filter (138) includes functionality to limit a user's view of the PHH account (114) to only the portion of the patient's PHH account (114) for which the user has been granted permission to access.

The following is an example of how a patient may use the system of FIG. 1. Specifically, in one or more embodiments of the invention, a patient may grant access to portions of the PHH accounts to healthcare providers treating the patient via a network connection, such as an online connection. The patient and/or healthcare provider may submit healthcare data, across the network, to the PHH account for review by another healthcare provider. Further, the healthcare provider may update healthcare data in the PHH account and thereby modify the health service of the patient. After the healthcare provider updates (or accesses) healthcare data, the patient may be sent an alert that new healthcare data is submitted (or is accessed). Accordingly, through a process of submitting and/or reviewing the new healthcare data, the health (i.e., medical) services of the patient may be effectively modified.

FIGS. 2-5 show flowcharts of methods for collaborative PHH in accordance with one or more embodiments of the invention. While the various steps in the flowcharts are presented and described sequentially, one of ordinary skill will appreciate that some or all of the steps may be executed in different orders and some or all of the steps may be executed in parallel.

Figure 2:
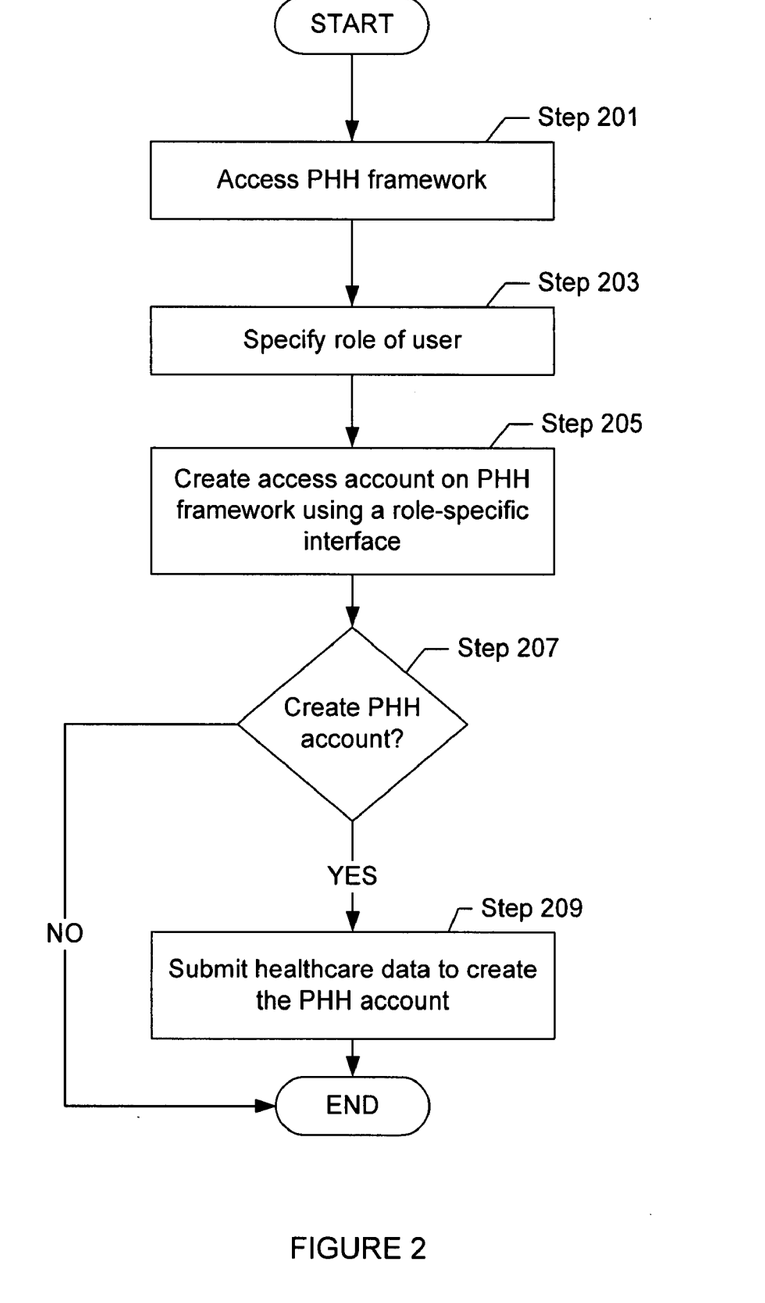
FIGS. 2-5 show flowcharts of methods for collaborative personal health history in accordance with one or more embodiments of the invention.

FIG. 2 shows a flowchart of a method for a user to create an access account with the healthcare framework in one or more embodiments of the invention. Initially, the user accesses the PHH framework (201). The user may access the PHH framework by entering a uniform resource identifier of the PHH framework in a web browser, by opening a client-side application stored locally on the user's device, or performing any other operation for accessing a remote system.

Next, the role of the user is specified (Step 203). The user may specify their role by enabling a link in a web browser or submitting data in an online form. Once the role is specified, the user creates an access account on the PHH framework using a role-specific interface (Step 205). The role-specific interface may lead the user through a series of questions specific to the role to create an access account. Alternatively, the role specific interface may have a form for a user to enter information into the access account.

Further, a determination is made whether to create a PHH account (Step 207). Specifically, if the user is a patient, the user may decide to create the PHH account and populate the PHH account with healthcare data at this time. If a determination is made to create the PHH account, then healthcare data is submitted to create and populate the PHH account (Step 209). The patient interface may include a mechanism for a user to directly submit healthcare data in the PHH account or authorize obtaining the healthcare data to populate PHH account from third parties.

For example, the patient interface may include a computer generated form with fields that a patient may user to enter the healthcare data. Alternatively, the patient interface may dynamically lead the user through a questionnaire to answer and populate the PHH account using the answers. For example, a question may be displayed asking whether the user has had any surgeries with radio buttons from which the user may select "yes" or "no". If the user selects "yes", then a question may be displayed which requests that the user enter specific information about the surgery, such as type, date, surgeon, etc.

Further, the patient interface may also or alternatively request information to authorize the PHH engine to populate the PHH account directly from medical records. For example, the patient may submit information granting permission to the PHH engine to obtain the PHH directly from the healthcare providers that are currently or have in the past treated the patient.

While not shown in FIG. 2, a user of the PHH framework may invite potential users to create an access account in order to collaborate on healthcare of the patient with the potential user. For example, a healthcare provider may invite a patient to create an access account and a PHH account before or after a first office visit. Conversely, after discovering that a healthcare provider or authorized individual does not have a PHH account, a patient may invite the healthcare provider or authorized individual to create an access account. The invite may include a temporary authentication mechanism, such as a token or a temporary login identifier and password. Further, the invite may be transmitted by the user or the PHH framework to an email address or physical address of the potential user. When a user has an access account, the user may use the role specific interface to collaborate on healthcare with other users.

Figure 3:
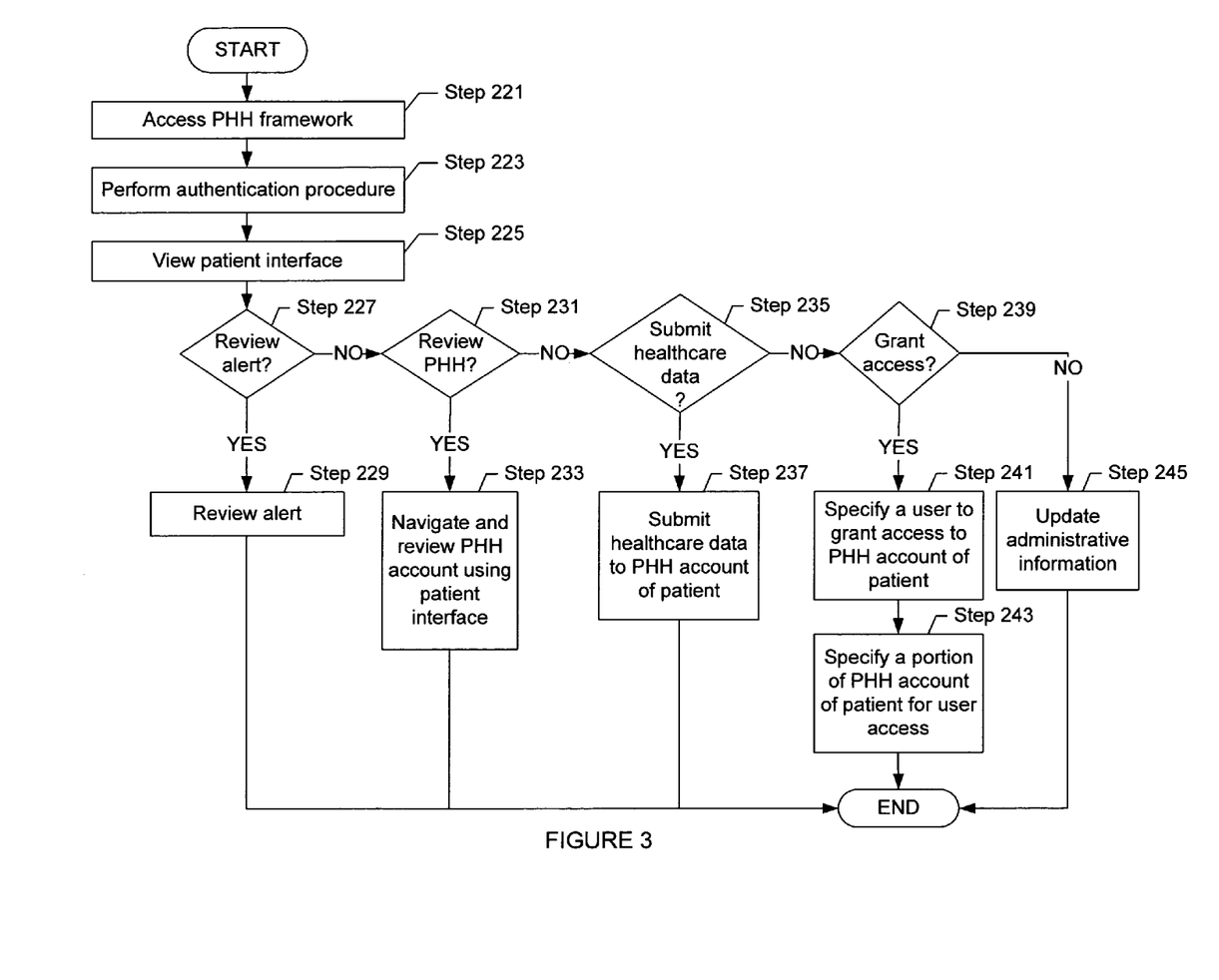

FIG. 3 shows a flowchart of a method for a patient to use the PHH account in one or more embodiments of the invention. Initially, the patient accesses the PHH framework (Step 221). The patient may access the PHH framework in the same manner as described in Step 201 of FIG. 2. Next, the patient performs an authentication procedure (Step 223). At this stage, the healthcare framework attempts to confirm the identity the patient. Thus, the authentication procedure may involve the patient entering a username, password, pin number, biometric data (e.g., a fingerprint), or any other procedure.

When the patient is authenticated, the patient may view a patient interface (Step 225). The patient interface guides the patient through interacting with the patient's PHH account. Using the patient interface, the patient may submit one or more requests to view and modify the healthcare data in the PHH account. The following is a few of the possible requests and actions that the patient may perform by submitting requests using the patient interface.

In one or more embodiments of the invention, the patient may determine whether to review alerts to the account (Step 227). The amounts and types of alerts may be configurable. For example, a patient may configure the patient's PHH account to display all alerts or only new alerts on the PHH account immediately after the patient is authenticated. The patient may further specify that all alerts, alerts from a particular healthcare provider, or alerts designated as high importance are to be immediately transmitted to the patient. For example, if the patient is waiting for a lab result and an analysis from a cardiologist, then the patient may specify that upon receiving healthcare data to the PHH account, an alert is to be sent to patient's cellular telephone.

If the patient decides to review an alert, then the alert is displayed and the patient reviews the alert (Step 229). The patient may further decide whether to perform an action based on the alert. For example, the patient may decide to forward the alert to an authorized individual or healthcare provider using the PHH framework. Specifically, the patient may grant the authorized individual or healthcare provider permission to access the alert. Alternatively, the patient may specify how the PHH framework may send the alert via short messaging service (SMS), email, or other transport mechanism to the authorized individual or healthcare provider.

Further, the alert may result in a modification of the healthcare of the patient. For example, if the alert is to indicate the results of a cardiologist report, the cardiologist may specify in the report that the patient needs to remove sodium from their diet. In another example, a healthcare provider may specify a new medication that the patient should use. Accordingly, the alert may be used as a collaboration technique which results in the modification of the health service of the patient.

Once the patient reviews the alert or if the patient determines not to review alerts, then the patient may determine whether to review the PHH (Step 231). If the patient decides to review their PHH, then the patient may navigate through the PHH account using the patient interface (Step 233). For example, the patient may request to view categories or a particular entry of healthcare data in the PHH account by clicking on a link, selecting a button, or submitting a command in the patient interface. In response, the patient interface may request the category or entry of healthcare data from the PHH repository. While a patient is reviewing their PHH, the patient may decide to alter their treatment plan based on a review of the healthcare data in the PHH account. For example, the patient may decide to switch healthcare providers, follow a suggestion of a healthcare provider, etc.

Similar to a patient reviewing the patient's PHH, an authorized individual may also navigate through and review the patient's PHH. However, the authorized individual may use an authorized individual interface which limits that which the authorized individual may view and prevents the authorized individual from granting access or modifying the patient's PHH.

Continuing with FIG. 3, while (or instead of) reviewing the PHH account, the patient may determine whether to submit healthcare data to the patient's PHH account (Step 235). Specifically, the patient may submit or modify healthcare data in the PHH account (Step 237). Submitting and modifying healthcare data may be performed as described above and in FIG. 2 when the PHH account is initially populated. The healthcare data in the PHH account may be updated at virtually anytime. For example, while monitoring an aspect of the patient's health and obtaining results (e.g., blood-sugar levels, temperature, blood pressure, pain, etc.), the patient may submit healthcare data to the PHH account. The patient may also modify healthcare data previously submitted to the PHH account.

Alternatively, the monitoring equipment may directly submit the data to the account. For example, a diabetic may configure the PHH account and a blood-sugar monitor transmits blood sugar levels to the PHH account to be reviewed by their endocrinologist. Similarly, a woman desiring pregnancy may submit morning temperature measurements via a thermometer to the PHH account for her obstetrician to review.

In addition or as an alternative to submitting healthcare data, the patient may determine whether to grant access to the PHH account (Step 239). In particular, the patient may desire to grant or revoke access to a user or a potential user of the PHH framework. In such scenario, the patient may specify a user for granting access (Step 241). Specifying a user may be performed by selecting a user in a drop-down menu, searching for a user in the PHH framework, or performing any other such action. For example, the patient may desire to add an acupuncturist. Accordingly, the patient may select acupuncturist specialty from a list of healthcare provider specialties. The selection of acupuncturist specialty may result in a second list of acupuncturists from which the user may make a selection.

In another example, a patient may desire to grant access to an authorized individual. In such scenario, the patient may search for the authorized individual using the name of the authorized individual or other identifying information in a search field in the patient interface.

If the patient is unable to find the authorized individual or healthcare provider, then the patient may determine that the authorized individual or healthcare provider is a potential user. Accordingly, the patient may invite the potential user to create an access account as described above. Alternatively, in one or more embodiments of the invention, the patient may specify that healthcare data may be transmitted to the potential user, such as via an email account of the potential user.

Continuing with FIG. 3, in addition to selecting a user or potential user, the patient may also specify a portion of the PHH account that the user or potential user may access (Step 243). At this stage, the patient may decide which healthcare data in the PHH account may be accessible by the user and which healthcare data is the user unauthorized to access. While specifying the portion of the PHH account, the patient may specify whether the user has both view and modify privileges. The patient may specify portions of the PHH account according to categories of the healthcare data or according to specific entries in the healthcare data. For example, the patient may grant access to all dental-related healthcare data and not grant access to podiatry-related treatments for a dental healthcare provider to access. Further, the patient may explicitly deny access to other portions of the PHH account, such as explicitly denying an authorized individual the ability to view medications treating infertility.

Multiple different methods may be performed to allow a patient to grant and deny access to portions of the PHH account. The following is only a few of the different mechanisms which may be used.

One method may involve the patient selecting specific entries in the healthcare data. For example, the patient may select checkboxes that are related to specific medications, surgeries, treatments, or conditions. In the example, the patient may specify using the checkboxes whether the user has both read and write access.

In another method, the patient may select categories of healthcare data in the PHH account. For example, the patient may select all medications, all surgeries, all lab results, or all entries generated for a particular healthcare provider or medical condition. The selection may be performed using checkboxes as described above or by using one or more links.

Alternatively, the patient may grant access by explicitly denying access to portions of the healthcare data. Specifically, the patient may specify that the user may access the entire healthcare account except for the portion specified by the patient. The patient may make the specification by selecting categories or checkboxes, as described above.

In another method, the user may request access to specific portions of the healthcare data. The request may be transmitted to the patient using email or other methods of notification. In response to the request, the patient may specify whether the user may access the account. For example, patient may grant a podiatrist privilege to request data from the account. In response, the podiatrist, or a podiatry assistant, may select different portions of the PHH account that would affect how the podiatrist manages the patient's health services. For example, the assistant may select medications, surgeries, and history of chronic illnesses without selecting urology related lab results. An email containing the selections may be transmitted to the patient. The email may request that the patient respond with granting access or denying access to the requested healthcare information. The patient may respond via email or using the PHH account.

The above is intended as only a few of the different mechanisms that may be used to grant access to healthcare data. One skilled in the art will appreciate that any number of equivalent methods may be performed.

Continuing with FIG. 3, the patient may also decide to update the administrative information (Step 245). Thus, the patient may navigate in the patient interface and update administrative information. For example, the patient may then modify address information, change the manner in which the patient interface is displayed, update alert notification (e.g., change how and when alerts are sent to the patient, change whether alerts are stored, etc.), or perform any other action related to updating administrative information for the PHH account.

While FIG. 3 shows an example of the different functions that may be performed by the patient, other operations and functions may also be performed. For example, using the PHH account the patient may send alerts and questions directly to the healthcare providers. For example, if the patient has pain in between office visits to a healthcare provider, the patient may notify the healthcare provider of the pain via the PHH framework. Thus, the healthcare provider may determine whether an immediate office visit or emergency room visit is required. As shown in the example, the PHH account provides another method for collaboration between the patient and the healthcare provider.

Figure 4:
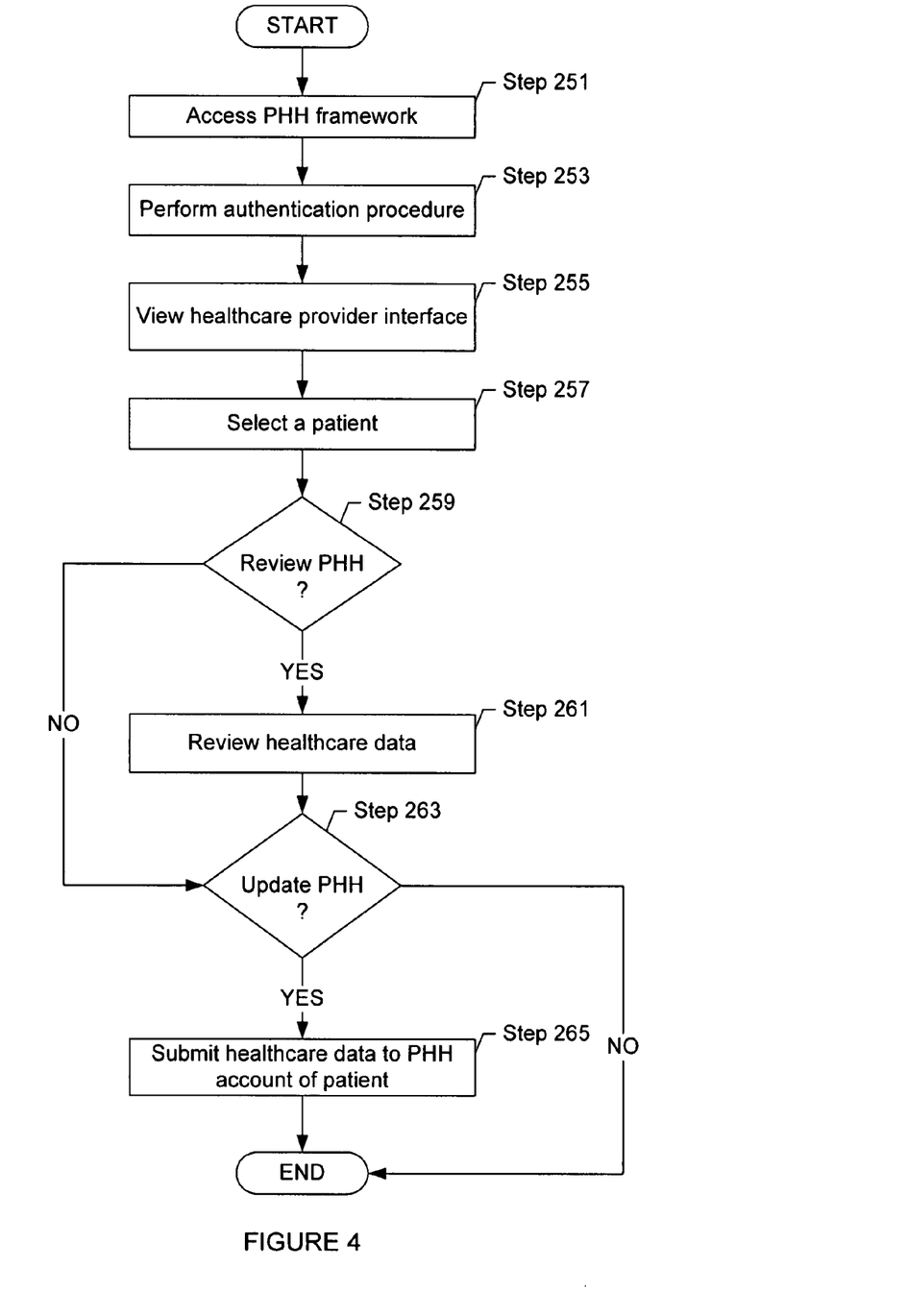

FIG. 4 shows a flowchart of a method for a healthcare provider to use the PHH account to collaborate on healthcare with the patient. Initially, the healthcare provider accesses the PHH framework (Step 251) and performs an authentication procedure (Step 253). Accessing the PHH framework and performing the authentication procedure may be performed in a manner similar to the patient accessing the PHH framework and performing the authentication procedure, as described in FIG. 3.

Once the healthcare provider performs the authentication procedure, the healthcare provider views a display via the healthcare provider interface (Step 255). In one or more embodiments of the invention, the healthcare provider interface is different from the patient interface because the healthcare provider may view portions of the PHH account of multiple patients.

In order to collaborate on healthcare with a particular patient, the healthcare provider may select a patient (Step 257). Specifically, the healthcare provider may use a name or other identifier to select a PHH account for a particular patient.

Further, the healthcare provider may determine whether to review the PHH (Step 259). Specifically, the healthcare provider may decide to review the patient's PHH before an office visit or if the patient contacts the healthcare provider.

If the healthcare provider decides to review the PHH, then the healthcare provider reviews the healthcare data in the PHH account (Step 261). Specifically, the healthcare provider may navigate through the portion of the PHH account for which the healthcare provider has been granted permission to access and subsequently review a display of the healthcare data. The healthcare provider may review the patient's PHH using the healthcare provider interface in a manner similar to the patient reviewing the patient's PHH using the patient interface. However, the healthcare provider may also be prevented from accessing certain portions of the patient's PHH.

While reviewing the patient's PHH, the healthcare provider may determine that the healthcare of the patient should be modified. For example, the healthcare provider may notice that the medications prescribed should be changed or that a different treatment plan is required. The healthcare provider may also suspend treatment or not perform a previously indicated medical procedure. In such scenario, the healthcare provider may modify the healthcare of the patient by not performing a previously medically indicated action.

For example, for a patient that has previously had an office visit with the healthcare provider, the patient and/or the healthcare provider may have defined a treatment plan to maintain or improve the health of the patient. Alternatively, the patient may have a treatment plan that the patient defined or that was defined with a different healthcare provider. When the healthcare provider, receives the healthcare data from the PHH account for the patient, the healthcare provider may review the healthcare data. Subsequently, based on the review, the healthcare provider may alter the treatment plan to modify the healthcare of the patient as described above.

While or instead of reviewing the PHH, the healthcare may determine whether to update the PHH (Step 263). For example, after an office visit, the healthcare provider may desire to submit prescriptions or notes about the office visit. If the healthcare provider decides to update the patient's PHH, then the healthcare provider submits healthcare data to the PHH account of the patient (Step 265). In one or more embodiments of the invention, the healthcare provider may submit healthcare data in a manner to the patient submitting healthcare data, as described above and in FIG. 3. The healthcare provider interface may limit the portion of the PHH account that the healthcare provider may modify and update. Further, in one or more embodiments of the invention, when the healthcare provider submits the healthcare data, the healthcare data is stored with an identifier of the healthcare provider.

Additionally, in one or more embodiments of the invention, the submission of healthcare data to the PHH account by the healthcare provider may be the release of healthcare data to the patient which is already stored in the PHH account. Specifically, one healthcare provider may submit healthcare data to the patient's PHH account to be viewed by a second healthcare provider. At this stage, the patient may not have access to the healthcare data from the first healthcare provider. The second healthcare provider may review the healthcare data from the first healthcare provider and release the healthcare data to the patient.

For example, if a blood sample from the patient is tested by the lab, the results from testing the blood sample may be stored in the patient's PHH account to be viewable only by the patient's physician who ordered the test. The patient's physician may review the results of the test and store notes about the test with the result. The patient's physician may then grant the patient access to the results of the test and the notes. While the patient, healthcare provider, and authorized individual are accessing the PHH account, the PHH engine is processing the requests and preventing unauthorized access to the PHH account and the PHH repository.

Figure 5:
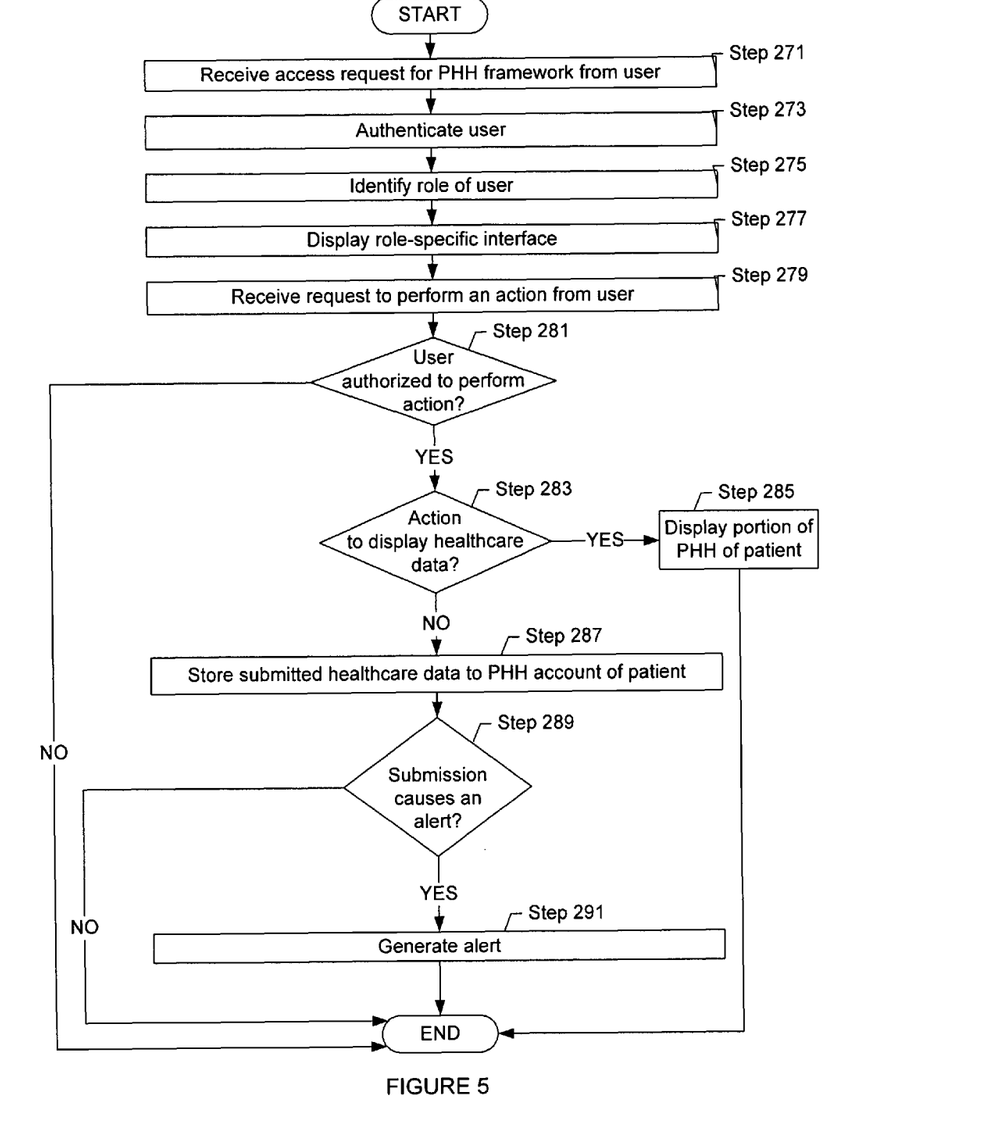

FIG. 5 shows a flowchart of a method for the PHH framework to process requests. Initially, the PHH framework receives an access request from a user (Step 271). The PHH framework may determine how to communicate with the user based on the access request. For example, the PHH framework may communicate with the user via SMS, a website, or other transport medium. Next, the PHH engine authenticates the user (Step 273). Specifically, after obtaining identifying information of the user (e.g., username, internet protocol (IP) address, etc.), the PHH engine may access the authentication and authorization account to find the access account for the user. Next, the PHH engine may verify the identity of the user using the access account of the user.

Further, the PHH engine may identify the role of the user (Step 275). The role of the user may be specified in the access account of the user. Based on the role of the user, the role specific interface for the user is displayed (Step 277). When displaying the role specific interface, information may be obtained from the access account of the user to display for the user. For example, the role-specific interface may display the name of the user and alerts.

Next, the PHH framework receives a request from the user to perform an action (Step 279). The request may be received by interpreting a command, which is submitted or receiving a selection in the role-specific interface. When the healthcare framework receives the request, a determination is made whether the user is authorized to perform the action (Step 281). Specifically, the authentication and authorization unit determines whether the action is permitted for the access account of the user. For example, if the request is to display the PHH account of a patient, the authentication and authorization unit may determine whether the user has permission to access the PHH account. In one or more embodiments of the invention, the authorization based filters may be configured to filter and therefore limit unauthorized transmission of information between the user and the PHH repository.

Accordingly, if the user is not authorized to perform the action, then the user may be informed of the lack of authorization and may request a different action (not shown).

Alternatively, if the user is authorized to perform the action, then a determination is made whether the action is for displaying the healthcare data (Step 283). If the action is to display the healthcare data, then the requested healthcare data is displayed (Step 285). Specifically, a query may be sent to the PHH repository for healthcare data that is in the PHH account of the patient. The PHH repository may respond to the query with the healthcare data. After the authentication and authorization unit verifies that the user is authorized to view the healthcare data, the PHH engine forwards the healthcare data to the user using the role-specific interface in one or more embodiments of the invention. Thus, the role-specific interface may display the healthcare data.

Displaying the healthcare data may involve transmitting the healthcare data to the user using any method known in the art. At this stage, the healthcare provider may view the portion of the healthcare data for which the healthcare provider has been granted permission to access.

If the action is not to display healthcare data, then the action may be to store health care data. In such scenario, the submitted healthcare data is stored in the PHH account of the patient (Step 287). Storing the submitted healthcare data may be performed by transmitting the healthcare data to the PHH repository. The PHH repository may perform a variety of techniques known in the art to ensure the autonomous storage of healthcare data.

Further, when storing the healthcare data, the PHH framework may consider whether the submission causes an alert (Step 289). The submission may be determined to trigger an alert when the user requests that an alert is created. For example, a patient may request that an authorized individual is alerted. In another example, a healthcare provider may request that another healthcare provider is alerted. Alternatively, the user preference may indicate whether submission of data results in an alert.

Accordingly, an alert is generated (Step 291). The alert may be generated, for example, by a user preference for the user to receive the alert. For example, if the alert is for the patient, the personal preferences of the patient may be accessed to determine how the patient is to receive the alert. For example, a message may be sent to the user via email or SMS or the alert may be stored in the PHH account for the patient. After or while generating the alert, the PHH framework may continue receiving requests for actions from the user. Further, in one or more embodiments of the invention, an alert is generated and transmitted in real-time when healthcare data is submitted. For example, it may appear that the patient receives the alert instantaneously upon the submission of the healthcare data by a healthcare provider In the following example, consider the scenario in which a patient under the care of a cardiologist and a neurologist and has a single pharmacist. While making an appointment for the first office visit to the cardiologist, an assistant to the cardiologist requests that the patient create a PHH account and grant the cardiologist access to the account. Specifically, the assistant gives the patient an IP address to use in a web browser. Thus, before the first office visit, at the patient's leisure, the patient creates the PHH account. Further, the patient answers a variety of healthcare questions using the patient interface. The patient then grants the cardiologist access to the portion of the PHH account relevant to the healthcare of the patient for the cardiologist.

During the first office visit, the cardiologist reviews the portion of the PHH data and conducts the office visit with the patient. Based on the portion of the PHH account, the cardiologist may administer a variety of tests to the patient and requests that the patient keep a daily journal of his/her exercise on the PHH account. Accordingly, the patient exercises and tracks the exercise in a journal in the medical notes section of the PHH account.

In the meantime, the patient creates an appointment to visit their neurologist. The patient determines that the neurologist is not listed as a healthcare provider in the PHH framework, so the patient sends an invite to the neurologist and grants the neurologist permission to the access the PHH account. The neurologist creates an access account based on the invite and reviews the patient's PHH. Next, the neurologist conducts an office visit and prescribes six medications for the patient. Next, the neurologist submits the prescriptions in the patient's PHH account.

Returning to the cardiologist, when the test results are analyzed, the cardiologist accesses the PHH account of the patient. Based on the journal and the test results, the cardiologist determines that the patient should take aspirin and maintain a low sodium diet. Accordingly, the cardiologist prescribes aspirin for the patient and adds aspirin to the list of medications and low-sodium diet to the notes. Further, the cardiologist submits the results of the test and the analysis to the PHH account. When the PHH account is updated with the data from the cardiologist, the patient is sent an alert.

After reviewing the alert, the patient decides to grant their spouse access to the cardiologist's submission in the PHH account. The patient may also decide to visit the pharmacist and purchase the aspirin and the six medications prescribed by the neurologist. The patient identifies the pharmacist as one of the healthcare providers who have access accounts in the PHH framework. Accordingly, the patient grants the pharmacist permission to view the medications in the PHH account of the patient.

Before filling the prescription, the pharmacist reviews the medications and realizes that aspirin conflicts with one of the six medications prescribed by the neurologist. Accordingly, the pharmacist sends an alert to the neurologist using the PHH framework. The PHH framework uses user preferences in the access account of the neurologist to determine that the method for sending the alert to the neurologist is via the neurologist's pager. Accordingly, the PHH framework sends the alert to the neurologist's pager.

The neurologist responds to the alert by calling the pharmacist and gives the pharmacist a new prescription, which removes the conflicting medication. Accordingly, the pharmacist fills the new prescription and sends the patient home with the aspirin and the new prescription.

By the time the patient arrives home, the patient's spouse has reviewed the results of the tests using the PHH framework. Accordingly, the patient's spouse prepares a low sodium dinner for the patient.

Figure 6:
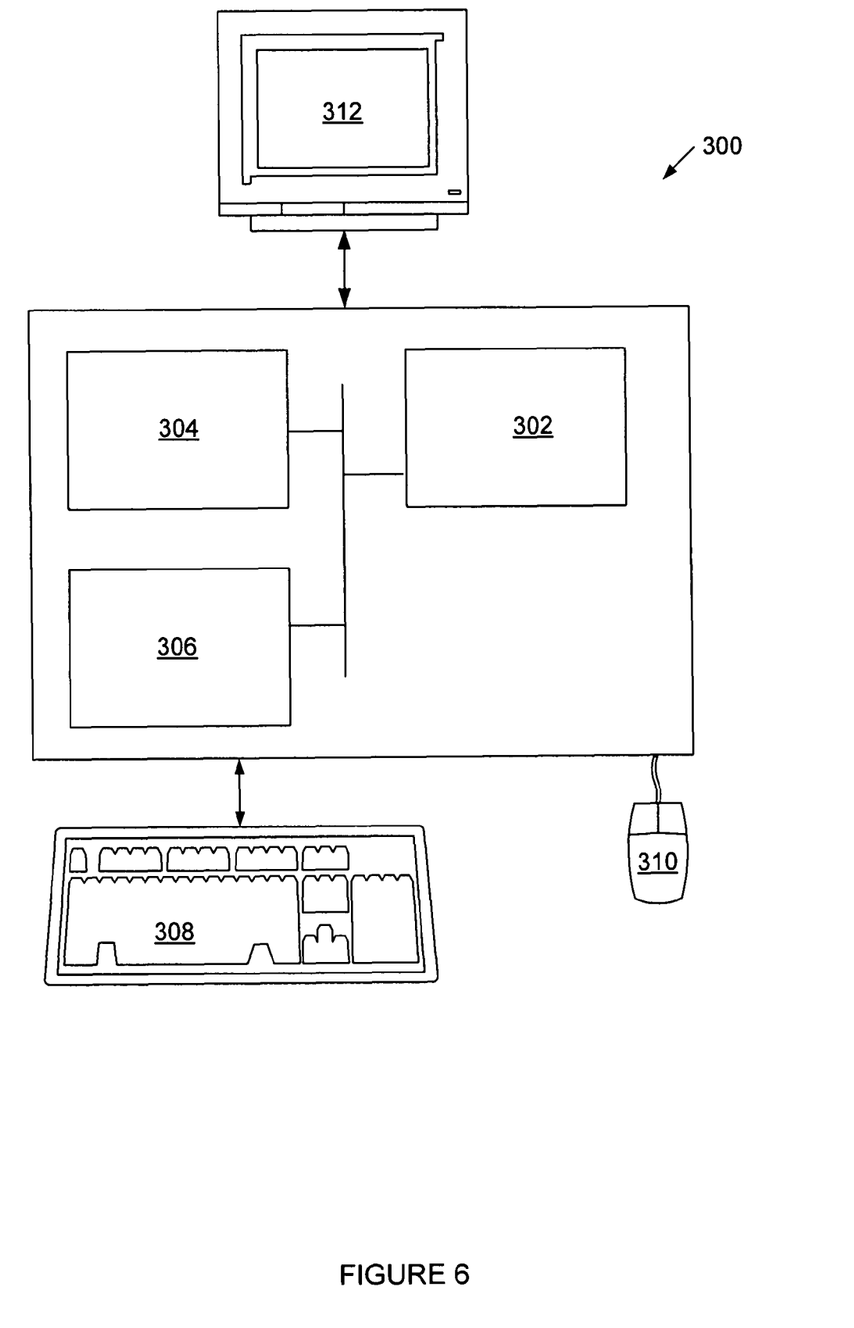
FIG. 6 shows a computer system in accordance with one or more embodiments of the invention.

The invention may be implemented on virtually any type of computer regardless of the platform being used. For example, as shown in FIG. 6, a computer system (300) includes a processor (302), associated memory (304), a storage device (306), and numerous other elements and functionalities typical of today's computers (not shown). The computer (300) may also include input means, such as a keyboard (308) and a mouse (310), and output means, such as a monitor (312). The computer system (300) is connected to a local area network (LAN) or a wide area network (e.g., the Internet) (not shown) via a network interface connection (not shown). Those skilled in the art will appreciate that these input and output means may take other forms.

Further, those skilled in the art will appreciate that one or more elements of the aforementioned computer system (300) may be located at a remote location and connected to the other elements over a network. Further, the invention may be implemented on a distributed system having a plurality of nodes, where each portion of the invention (e.g., patient's PHH, interfaces, authentication and authorization unit, etc.) may be located on a different node within the distributed system. In one embodiment of the invention, the node corresponds to a computer system. Alternatively, the node may correspond to a processor with associated physical memory. The node may alternatively correspond to a processor with shared memory and/or resources. Further, software instructions to perform embodiments of the invention may be stored on a computer readable medium such as a compact disc (CD), a diskette, a tape, a file, or any other computer readable storage device.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for healthcare collaboration comprising:
   receiving a first request from a patient to grant access, by a first healthcare provider, to a first portion of a personal health history (PHH) account associated with the patient;
   identifying a first healthcare provider's access account corresponding to the first healthcare provider;
   granting, by a computer processor and in response to the first request from the patient, access, across a network, to the first portion of the PHH account, wherein access is granted by providing the first healthcare provider's access account with permission to access the first portion of the PHH account, and wherein access is controlled by the patient;
   receiving, by the first portion of the PHH account and directly from a monitoring equipment, healthcare data obtained directly from the patient, wherein the monitoring equipment comprises at least one selected from a group consisting of a blood sugar monitor and a thermometer;
   transmitting, by the computer processor, the healthcare data obtained from the monitoring equipment to the first healthcare provider for review by the first healthcare provider;
   receiving, from the first healthcare provider, a healthcare report and a treatment plan based on a health service received by the patient from the first healthcare provider and based on the healthcare data, wherein the treatment plan comprises a first medication;
   storing, by the computer processor, the healthcare report and the treatment plan to the first portion of the PHH account;
   sending, by the computer processor, a first alert to the patient based on receiving the healthcare report for the patient from the first healthcare provider;
   determining that a second healthcare provider's access account corresponding to a second healthcare provider does not exist;
   sending, by the computer processor on behalf of the patient, an invite to the second healthcare provider to create the second healthcare provider's access account, wherein the invite comprises a token for temporary authentication of the second healthcare provider, and wherein the invite is sent in response to determining that the second healthcare provider's access account does not exist;
   creating, based on the invite and by the computer processor, the second healthcare provider's access account;
   receiving a second request from the patient to grant the second healthcare provider access only to a second portion of the PHH account, wherein the second portion comprises the healthcare report;
   granting, by the computer processor and based on the second request from the patient, access only to the second portion of the PHH account by providing the second healthcare provider's access account with permission to access only the second portion of the PHH account;
   transferring the healthcare report to the second healthcare provider for review;
   receiving to the treatment plan data indicating a second medication from the second healthcare provider
   transmitting data indicating the first medication and the second medication to a pharmacist with permission to access only medication data in the PHH account
   receiving a second alert from the pharmacist based on identification of a conflict between the first medication and the second medication;
   transmitting the second alert to the first healthcare provider; and
   altering the treatment plan by changing the first medication to a third medication based on a review of the second alert.

2. The method of claim 1, further comprising:
   receiving a request from the first healthcare provider to access the first portion of the PHH account; and
   transmitting the request from the first healthcare provider to the patient, wherein the first request from the patient is received in response to the request from the first healthcare provider.

3. The method of claim 1, further comprising:
   granting access to the healthcare report to an authorized individual by the patient; and
   reviewing the healthcare report by the authorized individual by accessing the PHH account.

4. The method of claim 1, wherein the first portion of the PHH account comprises a portion of healthcare data controlled by the patient and a portion of healthcare data controlled by the healthcare provider.

5. The method of claim 1, wherein the PHH account comprises data related to at least one selected from a group consisting of a diagnosis and a medical note.

6. The method of claim 1, wherein the second healthcare provider is at least one selected from a group consisting of a physician, a hospital, a clinic, a paramedic, a nurse, and a medical technician.

7. A system for healthcare collaboration comprising:
   a personal health history (PHH) repository for storing a PHH account associated with a patient; and a computer processor configured to:
   receive a first request from the patient to grant access, by a first healthcare provider, to a first portion of the PHH account;
   identify a first healthcare provider's access account corresponding to the first healthcare provider;
   grant access, across a network in response to the first request from the patient, to the first portion of the PHH account, wherein access is granted by providing the first healthcare provider's access account with permission to access the first portion of the PHH account, and wherein access is controlled by the patient;

receive, for the first portion of the PHH account and directly from a monitoring equipment, healthcare data obtained directly from the patient, wherein the monitoring equipment comprises at least one selected from a group consisting of a blood sugar monitor and a thermometer;

transmit the healthcare data obtained from the monitoring equipment to the first healthcare provider for review by the first healthcare provider;

receive, from the first healthcare provider, a healthcare report and a treatment plan based on a health service received by the patient from the first healthcare provider and based on the healthcare data, wherein the treatment plan comprises a first medication;

populate the first portion of the PHH account with healthcare report and the treatment plan;

send, by the computer processor, an alert to the patient based on receiving the healthcare report for the patient from the first healthcare provider;

determine that a second healthcare provider's access account corresponding to a second healthcare provider does not exist;

send, on behalf of the patient, an invite to the second healthcare provider to create the second healthcare provider's access account, wherein the invite comprises a token for temporary authentication of the second healthcare provider, and wherein the invite is sent in response to determining that the second healthcare provider's access account does not exist;

create, based on the invite, the second healthcare provider's access account;

receive a second request from the patient to grant the second healthcare provider access only to a second portion of the PHH account, wherein the second portion comprises the healthcare report;

grant, by the computer processor and based on the second request from the patient, access only to the second portion of the PHH account by providing the second healthcare provider's access account with permission to access only the second portion of the PHH account;

display the healthcare report to the second healthcare provider when the second healthcare provider accesses the PHH account;

receive to the treatment plan data indicating a second medication from the second healthcare provider transmit data indicating the first medication and the second medication to a pharmacist with permission to access only medication data in the PHH account receive a second alert from the pharmacist based on identification of a conflict between the first medication and the second medication;

transmit the second alert to the first healthcare provider; and alter the treatment plan by changing the first medication to a third medication based on a review of the second alert.

8. The system of claim 7, wherein the computer processor is further configured to:
receive a request from the first healthcare provider to access the first portion of the PHH account; and
transmit the request from the first healthcare provider to the patient, wherein the first request from the patient is received in response to the request from the first healthcare provider.

9. The system of claim 7, further comprising:
a healthcare provider interface for displaying the healthcare data for the first healthcare provider; and
a patient interface for receiving data from the patient.

10. The system of claim 7, wherein the computer processor is further configured to:
create the second healthcare provider's access account to access the PHH account of the patient; and
limit access by the healthcare provider to only the second portion of the PHH account.

11. The system of claim 7, further comprising:
an authorized individual interface for allowing an authorized individual to review healthcare data by accessing the PHH account.

12. The system of claim 7, the PHH account comprises data related to at least one selected from a group consisting of a medication, a diagnosis, and a medical note.

13. The system of claim 7, wherein the healthcare provider is at least one selected from a group consisting of a physician, a hospital, a clinic, a paramedic, a nurse, and a medical technician.

14. A non-transitory computer readable medium having tangibly embodied instructions stored thereon that when executed cause a computer processor to perform a method, the method comprising the steps of:
receiving a first request from a patient to grant access, by a first healthcare provider, to a first portion of a personal health history (PHH) account associated with the patient;
identifying a first healthcare provider's access account;
granting, in response to the first request from the patient, access, across a network, to the first portion of the PHH account, wherein access is granted by providing the first healthcare provider's access account with permission to access the first portion of the PHH account, and wherein access is controlled by the patient;
receiving, by the first portion of the PHH account and directly from a monitoring equipment, healthcare data obtained directly from the patient, wherein the monitoring equipment comprises at least one selected from a group consisting of a blood sugar monitor and a thermometer;
transmitting the healthcare data obtained from the monitoring equipment to the first healthcare provider for review by the first healthcare provider;
receiving, from the first healthcare provider, a healthcare report and a treatment plan based on a health service received by the patient from the first healthcare provider and based on the healthcare data, wherein the treatment plan comprises a first medication;
storing the healthcare report to the first portion of the PHH account;
sending a first alert to the patient based on receiving the healthcare report for the patient from the first healthcare provider;
determining that a second healthcare provider's access account corresponding to a second healthcare provider does not exist;
sending, by the computer processor on behalf of the patient, an invite to the second healthcare provider to create the second healthcare provider's access account, wherein the invite comprises a token for temporary authentication of the second healthcare provider, and wherein the invite is sent in response to determining that the second healthcare provider's access account does not exist;

creating, based on the invite, the second healthcare provider's access account;

receiving a second request from the patient to grant the second healthcare provider access only to a second portion of the PHH account, wherein the second portion comprises the healthcare report;

granting, based on the second request from the patient, access only to the second portion of the PHH account by providing the second healthcare provider's access account with permission to access only the second portion of the PHH account;

receiving to the treatment plan data indicating a second medication from the second healthcare provider transmitting data indicating the first medication and the second medication to a pharmacist with permission to access only medication data in the PHH account receiving a second alert from the pharmacist based on identification of a conflict between the first medication and the second medication;

transmitting the second alert to the first healthcare provider; and altering the treatment plan by changing the first medication to a third medication based on a review of the second alert.

15. The non-transitory computer readable medium of claim 14, wherein the method further comprises:

receiving a request from the first healthcare provider to access the first portion of the PHH account; and transmitting the request from the first healthcare provider to the patient, wherein the first request from the patient is received in response to the request from the first healthcare provider.

* * * * *

UNITED STATES PATENT AND TRADEMARK OFFICE
CERTIFICATE OF CORRECTION

| | | |
|---|---|---|
| PATENT NO. | : 7,983,934 B1 | Page 1 of 1 |
| APPLICATION NO. | : 11/796627 | |
| DATED | : July 19, 2011 | |
| INVENTOR(S) | : Steven A. Sholtis et al. | |

It is certified that error appears in the above-identified patent and that said Letters Patent is hereby corrected as shown below:

In Claim 1, Column 16 (line 19), there should be a ";" after "provider".

In Claim 1, Column 16 (line 22), there should be a ";" after "account".

In Claim 14, Column 19 (line 12), the following should be added after the ";" transferring the healthcare report to the second healthcare provider for review;

Signed and Sealed this
Twenty-fifth Day of October, 2011

David J. Kappos
*Director of the United States Patent and Trademark Office*